(12) United States Patent
Gipmans et al.

(10) Patent No.: US 7,465,850 B2
(45) Date of Patent: Dec. 16, 2008

(54) USE OF A GENE FOR INCREASING THE OIL CONTENT IN PLANTS

(75) Inventors: Martijn Gipmans, Potsdam (DE); Anders Dahlqvist, Furulund (SE); Antoni Banas, Siedlce (PL); Ulf Stahl, Uppsala (SE); Eva Wiberg, Uppsala (SE); Marit Lenman, Lund (SE); Hans Ronne, Uppsala (SE); Sten Stymne, Svalöv (SE)

(73) Assignee: BASF Plant Science GmbH (DE)

( * ) Notice: Subject to any disclaimer, the term of this patent is extended or adjusted under 35 U.S.C. 154(b) by 236 days.

(21) Appl. No.: 10/519,943

(22) PCT Filed: Jul. 3, 2003

(86) PCT No.: PCT/EP03/07084

§ 371 (c)(1),
(2), (4) Date: Dec. 29, 2004

(87) PCT Pub. No.: WO2004/007727

PCT Pub. Date: Jan. 22, 2004

(65) Prior Publication Data

US 2006/0174373 A1    Aug. 3, 2006

(30) Foreign Application Priority Data

Jul. 10, 2002    (EP)    ................... 02015344

(51) Int. Cl.
*C12N 15/31*    (2006.01)
*C12N 15/82*    (2006.01)
*C12N 15/63*    (2006.01)
*C12N 5/14*    (2006.01)
*A01H 5/00*    (2006.01)
*A01H 5/10*    (2006.01)

(52) U.S. Cl. .................. 800/281; 800/288; 800/295; 800/298; 435/468; 435/410; 435/320.1; 536/23.2; 536/23.74

(58) Field of Classification Search .................. 800/281
See application file for complete search history.

(56) References Cited

FOREIGN PATENT DOCUMENTS

WO    WO/00/60095    12/2000

OTHER PUBLICATIONS

Post-Beittenmiller, et al., (1989) Expression Of Holo And Apo Forms Of Spinach Acyl Carrier Protein-1 In Leaves Of Transgenic Tobacco Plants. Plant Cell 1:889-899.*
Voelker, et al (2001). Variations in the biosynthesis of seed-storage lipids. Annu. Rev. Plant Physiol. Plant Mol. Biol. 52, 335-361.*
Doerks, et al (1998) Protein Annotation: Detective Work For Function Prediction TIG 14(6) 248-250.*
Stephanopolous et al. Metabolic Engineering—Methodologies And Future Prospects TIBTECH 11:392-396.*
Ramezani, et al.(Identity Nuc. Database. Accession Z49598 Y13136, locus SCYJR098C, Aug. 11, 1997.*
Bauer, et al (GenEBML Database Accession No. AX594852, Feb. 14, 2003).*
Lichtenberg (2005) Yeast 22:1191-1201).*
Frentzen, Margrit, "Acyltransferases from Basic Science to Modified Seed Oils," *Lipids*, 100:161-166 (1998).
Ohlrogge, John, et al., "Lipid Biosynthesis," *The Plant Cell*, 7:957-970 (1995).
Sandager, Line, et al., "Storage Lipid Synthesis is Non-Essential in Yeast," *The Journal of Biological Chemistry*, 277(8):6478-6482 (2002).
Topfer, Reinhard, et al., "Modification of Plant Lipid Synthesis," *Science*, 268:681-686 (1995).
Database Accession No. Z49598.
Database Accession No. P47139.

* cited by examiner

*Primary Examiner*—Anne Marie Grunberg
*Assistant Examiner*—Brent Page
(74) *Attorney, Agent, or Firm*—Connolly Bove Lodge & Hutz LLP

(57) ABSTRACT

The invention relates to methods for increasing the oil content in plants, preferably in plant seeds, by expressing a polypeptide from yeast. The invention furthermore relates to expression constructs for expressing the yeast polypeptide in plants, preferably in plant seeds, the transgenic plants expressing the yeast polypeptide and to the use of said transgenic plants for the production of food, feeds, seed, pharmaceuticals or fine chemicals, in particular for the production of oils.

19 Claims, No Drawings

SEQUENCE LISTING

```
<160> NUMBER OF SEQ ID NOS: 2

<210> SEQ ID NO 1
<211> LENGTH: 2439
<212> TYPE: DNA
<213> ORGANISM: Saccharomyces cerevisiae
<220> FEATURE:
<221> NAME/KEY: CDS
<222> LOCATION: (30)..(1994)

<400> SEQUENCE: 1
cttgtagagg ttaactgggg agtattaca atg atg gca act ccg gct act gat        53
                                Met Met Ala Thr Pro Ala Thr Asp
                                  1               5 ctt att tcc gat aat gat aaa tat aac aag caa tgt ctt tct gat tca       101
Leu Ile Ser Asp Asn Asp Lys Tyr Asn Lys Gln Cys Leu Ser Asp Ser
         10                  15                  20 agt gat agt ggt agt gat gta agc ttt ttt tcc gta aat gaa agc gaa       149
Ser Asp Ser Gly Ser Asp Val Ser Phe Phe Ser Val Asn Glu Ser Glu
 25                  30                  35                  40 ggt gaa ttg gat aca atg gag aaa gtg gat acc ttg att gga ggt gca       197
Gly Glu Leu Asp Thr Met Glu Lys Val Asp Thr Leu Ile Gly Gly Ala
                 45                  50                  55 aga gtt ata agc aat aaa gta gaa aaa gac agc gat agt gaa caa agg       245
Arg Val Ile Ser Asn Lys Val Glu Lys Asp Ser Asp Ser Glu Gln Arg
             60                  65                  70 gga aga aag aag gaa aca act ggg ccc aat aac tat cat aat tta gaa       293
Gly Arg Lys Lys Glu Thr Thr Gly Pro Asn Asn Tyr His Asn Leu Glu
         75                  80                  85 gag aag caa gcg agt gcc att tct ctt gac gct gat gat gaa gat ctc       341
Glu Lys Gln Ala Ser Ala Ile Ser Leu Asp Ala Asp Asp Glu Asp Leu
     90                  95                 100 gat gaa att att tct tat tcg cat gac ggg aac tat gac agc tct cat       389
Asp Glu Ile Ile Ser Tyr Ser His Asp Gly Asn Tyr Asp Ser Ser His
105                 110                 115                 120 aaa act ttc tcc ttt tcc tta cca ttt ggt aat aca aat ttc cga tca       437
Lys Thr Phe Ser Phe Ser Leu Pro Phe Gly Asn Thr Asn Phe Arg Ser
                125                 130                 135 agt tca cca tta gcc ata att aaa act gtg ctt ccc aag act cca gat       485
Ser Ser Pro Leu Ala Ile Ile Lys Thr Val Leu Pro Lys Thr Pro Asp
            140                 145                 150 gag ttc atc aaa aag aat cta aga aag aat gag atc aag caa aaa ctg       533
Glu Phe Ile Lys Lys Asn Leu Arg Lys Asn Glu Ile Lys Gln Lys Leu
        155                 160                 165 aaa aaa tca acc tcc att tct tcc ttg gaa gag ata gaa tta ttt aaa       581
Lys Lys Ser Thr Ser Ile Ser Ser Leu Glu Glu Ile Glu Leu Phe Lys
    170                 175                 180
```

-continued

| | |
|---|---|
| tac gaa agg ggc att gat aat tca agg tta agg gct gtt aaa gaa tct<br>Tyr Glu Arg Gly Ile Asp Asn Ser Arg Leu Arg Ala Val Lys Glu Ser<br>185                    190                      195                    200 | 629 |
| ttg gaa atg gat gcc ttg aag aac tcc att aag caa ata aca gca gac<br>Leu Glu Met Asp Ala Leu Lys Asn Ser Ile Lys Gln Ile Thr Ala Asp<br>                    205                      210                    215 | 677 |
| cca ttc gac aaa act cat gac gga tat tac cgt tcg cgt tta gaa tct<br>Pro Phe Asp Lys Thr His Asp Gly Tyr Tyr Arg Ser Arg Leu Glu Ser<br>          220                      225                    230 | 725 |
| ata tgg aat gaa ttg gaa gga gat gtc gtt ata atg ggt gga tat cga<br>Ile Trp Asn Glu Leu Glu Gly Asp Val Val Ile Met Gly Gly Tyr Arg<br>      235                      240                    245 | 773 |
| ggt agt gtg cta agg gat gct act act cat aag cga att tgg atc cca<br>Gly Ser Val Leu Arg Asp Ala Thr Thr His Lys Arg Ile Trp Ile Pro<br>250                    255                      260 | 821 |
| tta aag gca ggt ttg aat atg acg aaa gtc gat tta ttg atc gga cct<br>Leu Lys Ala Gly Leu Asn Met Thr Lys Val Asp Leu Leu Ile Gly Pro<br>265                    270                    275                    280 | 869 |
| aat gac gaa gat gaa ctt aaa act cag aag gag att gtc cct gat gga<br>Asn Asp Glu Asp Glu Leu Lys Thr Gln Lys Glu Ile Val Pro Asp Gly<br>                    285                      290                    295 | 917 |
| atg cta aca cat ata ggg cct gtt gat atc tct aag agg ttg ata aag<br>Met Leu Thr His Ile Gly Pro Val Asp Ile Ser Lys Arg Leu Ile Lys<br>          300                      305                    310 | 965 |
| agg cta gac gca aat cct aat tta aat gtt cag cag ttt ggc tat gat<br>Arg Leu Asp Ala Asn Pro Asn Leu Asn Val Gln Gln Phe Gly Tyr Asp<br>      315                      320                    325 | 1013 |
| tgg aga tta tcc ttg gac ata tct gcc aag cat tta acg act aaa cta<br>Trp Arg Leu Ser Leu Asp Ile Ser Ala Lys His Leu Thr Thr Lys Leu<br>330                    335                      340 | 1061 |
| gag gaa att tac aat aag caa aaa aat aag aag gga ata tac atc att<br>Glu Glu Ile Tyr Asn Lys Gln Lys Asn Lys Lys Gly Ile Tyr Ile Ile<br>345                    350                    355                    360 | 1109 |
| gcc cat tca atg ggc gga ttg gtc gca cat aaa gtg ttg caa gac tgt<br>Ala His Ser Met Gly Gly Leu Val Ala His Lys Val Leu Gln Asp Cys<br>                    365                      370                    375 | 1157 |
| act cat ttg ata aga ggt att att tac gtg ggt tcc cca agc caa tgt<br>Thr His Leu Ile Arg Gly Ile Ile Tyr Val Gly Ser Pro Ser Gln Cys<br>          380                      385                    390 | 1205 |
| cca aat att tta ggt cct att agg ttt gga gat gat gtg atg tgg aat<br>Pro Asn Ile Leu Gly Pro Ile Arg Phe Gly Asp Asp Val Met Trp Asn<br>      395                      400                    405 | 1253 |
| aaa cta ttt tca cta aga acc aac ttt ttt atg aga agt agt ttc tat<br>Lys Leu Phe Ser Leu Arg Thr Asn Phe Phe Met Arg Ser Ser Phe Tyr<br>410                    415                      420 | 1301 |
| ttt cta ccg tta gat ggt aga tgt ttt gtt gac aaa att acc tta gag<br>Phe Leu Pro Leu Asp Gly Arg Cys Phe Val Asp Lys Ile Thr Leu Glu<br>425                    430                      435                    440 | 1349 |
| agg tat gat ttc gat ttt ttt gat aca gat gtt tgg aaa acc ctt ggc<br>Arg Tyr Asp Phe Asp Phe Phe Asp Thr Asp Val Trp Lys Thr Leu Gly<br>                    445                      450                    455 | 1397 |
| ttg tca cct ctc gtc aat gag aaa aga gag gaa tca gct cac gaa aaa<br>Leu Ser Pro Leu Val Asn Glu Lys Arg Glu Glu Ser Ala His Glu Lys<br>          460                      465                    470 | 1445 |
| tca aaa tta tta cca agg aaa acg aaa tca gcg ctt tcg ctt aaa gct<br>Ser Lys Leu Leu Pro Arg Lys Thr Lys Ser Ala Leu Ser Leu Lys Ala<br>      475                      480                    485 | 1493 |
| acc cta aac gca act acc aag ttt gtc cta aat gca cct gtt gtt agg<br>Thr Leu Asn Ala Thr Thr Lys Phe Val Leu Asn Ala Pro Val Val Arg | 1541 |

```
                        490                   495                    500
aat gta gcc ggc aat aat aaa cag gta cca agg gat gtg cct ttc gat       1589
Asn Val Ala Gly Asn Asn Lys Gln Val Pro Arg Asp Val Pro Phe Asp
505                 510                 515                 520 gaa gtc ttc cat aca tct tat gaa gat agc tgt gaa tat tta gcg aga       1637
Glu Val Phe His Thr Ser Tyr Glu Asp Ser Cys Glu Tyr Leu Ala Arg
                525                 530                 535 act tta aaa cgt aca aag aat tat ttg gat agc tta gat tac gac ccg       1685
Thr Leu Lys Arg Thr Lys Asn Tyr Leu Asp Ser Leu Asp Tyr Asp Pro
            540                 545                 550 aac aaa gaa tat cct cca ttg gcc atg gtt tac ggt aac aag gtt ccc       1733
Asn Lys Glu Tyr Pro Pro Leu Ala Met Val Tyr Gly Asn Lys Val Pro
        555                 560                 565 act gtt aga ggt gct aaa gtg aac ggt ata caa gat ata aaa gat ggg       1781
Thr Val Arg Gly Ala Lys Val Asn Gly Ile Gln Asp Ile Lys Asp Gly
    570                 575                 580 aat tat gaa gat ttt tac tat ggt ccg ggc gac ggt gtt gtt cac cat       1829
Asn Tyr Glu Asp Phe Tyr Tyr Gly Pro Gly Asp Gly Val Val His His
585                 590                 595                 600 aaa tgg tta ttg cct gaa cag aga ggc ttt cca gtt gtt tgt aaa atc       1877
Lys Trp Leu Leu Pro Glu Gln Arg Gly Phe Pro Val Val Cys Lys Ile
                605                 610                 615 gcc agt tct tca ggt cat gtt agc tta atg acg gat ttg aaa tca atg       1925
Ala Ser Ser Ser Gly His Val Ser Leu Met Thr Asp Leu Lys Ser Met
            620                 625                 630 gca aaa gca ttc ata tct atc gtc gac agc gaa aaa gaa gga aga aga       1973
Ala Lys Ala Phe Ile Ser Ile Val Asp Ser Glu Lys Glu Gly Arg Arg
        635                 640                 645 tct cga aca cga act tct tca tgaaaggctt tttattcctt tgtttactat         2024
Ser Arg Thr Arg Thr Ser Ser
    650                 655 tcatatctgc attttctttt ttaccaaaat tccgcatgtc aaaaaaaatc tggcaacgca    2084
ccgcgaataa aaataaataa tatttttta tctttagttg cctaaatact atttatttcg     2144
tcaattttac aacctctttt atatacacca ttcgatttcc cacgaagtaa aataataatt    2204
ctataaacag atttatctga tatgctcaat ttcccctccc attttcatta ttgtccttct    2264
tgctcttcct cgatgtcaaa attaaccttc agccataagc tgcatgcgct acattgggtt    2324
aataattgat aaccagaatg actccgttcc atagcgtcta cattatcaat gcattcatct    2384
aacaaactct cactaaaatg aaaccacca acaaattgac agcgaggaca attca          2439
```

<210> SEQ ID NO 2
<211> LENGTH: 655
<212> TYPE: PRT
<213> ORGANISM: Saccharomyces cerevisiae

<400> SEQUENCE: 2

```
Met Met Ala Thr Pro Ala Thr Asp Leu Ile Ser Asp Asn Asp Lys Tyr
 1               5                  10                  15

Asn Lys Gln Cys Leu Ser Asp Ser Ser Asp Ser Gly Ser Asp Val Ser
            20                  25                  30

Phe Phe Ser Val Asn Glu Ser Glu Gly Glu Leu Asp Thr Met Glu Lys
        35                  40                  45

Val Asp Thr Leu Ile Gly Gly Ala Arg Val Ile Ser Asn Lys Val Glu
    50                  55                  60

Lys Asp Ser Asp Ser Glu Gln Arg Gly Arg Lys Lys Glu Thr Thr Gly
65                  70                  75                  80
```

```
Pro Asn Asn Tyr His Asn Leu Glu Glu Lys Gln Ala Ser Ala Ile Ser
                85                  90                  95
Leu Asp Ala Asp Asp Glu Asp Leu Asp Glu Ile Ile Ser Tyr Ser His
            100                 105                 110
Asp Gly Asn Tyr Asp Ser Ser His Lys Thr Phe Ser Phe Ser Leu Pro
        115                 120                 125
Phe Gly Asn Thr Asn Phe Arg Ser Ser Ser Pro Leu Ala Ile Ile Lys
    130                 135                 140
Thr Val Leu Pro Lys Thr Pro Asp Glu Phe Ile Lys Lys Asn Leu Arg
145                 150                 155                 160
Lys Asn Glu Ile Lys Gln Lys Leu Lys Lys Ser Thr Ser Ile Ser Ser
                165                 170                 175
Leu Glu Glu Ile Glu Leu Phe Lys Tyr Glu Arg Gly Ile Asp Asn Ser
            180                 185                 190
Arg Leu Arg Ala Val Lys Glu Ser Leu Glu Met Asp Ala Leu Lys Asn
        195                 200                 205
Ser Ile Lys Gln Ile Thr Ala Asp Pro Phe Asp Lys Thr His Asp Gly
    210                 215                 220
Tyr Tyr Arg Ser Arg Leu Glu Ser Ile Trp Asn Glu Leu Glu Gly Asp
225                 230                 235                 240
Val Val Ile Met Gly Gly Tyr Arg Gly Ser Val Leu Arg Asp Ala Thr
                245                 250                 255
Thr His Lys Arg Ile Trp Ile Pro Leu Lys Ala Gly Leu Asn Met Thr
            260                 265                 270
Lys Val Asp Leu Leu Ile Gly Pro Asn Asp Glu Asp Glu Leu Lys Thr
        275                 280                 285
Gln Lys Glu Ile Val Pro Asp Gly Met Leu Thr His Ile Gly Pro Val
    290                 295                 300
Asp Ile Ser Lys Arg Leu Ile Lys Arg Leu Asp Ala Asn Pro Asn Leu
305                 310                 315                 320
Asn Val Gln Gln Phe Gly Tyr Asp Trp Arg Leu Ser Leu Asp Ile Ser
                325                 330                 335
Ala Lys His Leu Thr Thr Lys Leu Glu Glu Ile Tyr Asn Lys Gln Lys
            340                 345                 350
Asn Lys Lys Gly Ile Tyr Ile Ile Ala His Ser Met Gly Gly Leu Val
        355                 360                 365
Ala His Lys Val Leu Gln Asp Cys Thr His Leu Ile Arg Gly Ile Ile
    370                 375                 380
Tyr Val Gly Ser Pro Ser Gln Cys Pro Asn Ile Leu Gly Pro Ile Arg
385                 390                 395                 400
Phe Gly Asp Asp Val Met Trp Asn Lys Leu Phe Ser Leu Arg Thr Asn
                405                 410                 415
Phe Phe Met Arg Ser Ser Phe Tyr Phe Leu Pro Leu Asp Gly Arg Cys
            420                 425                 430
Phe Val Asp Lys Ile Thr Leu Glu Arg Tyr Asp Phe Asp Phe Phe Asp
        435                 440                 445
Thr Asp Val Trp Lys Thr Leu Gly Leu Ser Pro Leu Val Asn Glu Lys
    450                 455                 460
Arg Glu Glu Ser Ala His Glu Lys Ser Lys Leu Leu Pro Arg Lys Thr
465                 470                 475                 480
Lys Ser Ala Leu Ser Leu Lys Ala Thr Leu Asn Ala Thr Thr Lys Phe
                485                 490                 495
Val Leu Asn Ala Pro Val Val Arg Asn Val Ala Gly Asn Asn Lys Gln
```

-continued

```
                        500                 505                 510
Val Pro Arg Asp Val Pro Phe Asp Glu Val Phe His Thr Ser Tyr Glu
            515                 520                 525

Asp Ser Cys Glu Tyr Leu Ala Arg Thr Leu Lys Arg Thr Lys Asn Tyr
            530                 535                 540

Leu Asp Ser Leu Asp Tyr Asp Pro Asn Lys Glu Tyr Pro Pro Leu Ala
545                         550                 555                 560

Met Val Tyr Gly Asn Lys Val Pro Thr Val Arg Gly Ala Lys Val Asn
                    565                 570                 575

Gly Ile Gln Asp Ile Lys Asp Gly Asn Tyr Glu Asp Phe Tyr Tyr Gly
                580                 585                 590

Pro Gly Asp Gly Val Val His His Lys Trp Leu Leu Pro Glu Gln Arg
            595                 600                 605

Gly Phe Pro Val Val Cys Lys Ile Ala Ser Ser Ser Gly His Val Ser
        610                 615                 620

Leu Met Thr Asp Leu Lys Ser Met Ala Lys Ala Phe Ile Ser Ile Val
625                 630                 635                 640

Asp Ser Glu Lys Glu Gly Arg Arg Ser Arg Thr Arg Thr Ser Ser
                    645                 650                 655
```

USE OF A GENE FOR INCREASING THE OIL CONTENT IN PLANTS

RELATED APPLICATIONS

This application is a national stage application (under 35 U.S.C. 371) of PCT/EP2003/007084 filed Jul. 3, 2003, which claims benefit of European application 02015344.1 filed Jul. 10, 2002.

The invention relates to the use of a gene that when expressed will increase the total amount of oil (i.e. triacylglycerols—TAG) that is produced in transgenic organisms.

More specifically this invention describes the identification of a gene encoding a TAG synthesis enhancing protein (TEP).

In a first embodiment, this invention is directed to the TEP protein comprising an amino acid sequence as set forth in SEQ ID NO: 2 or a functional fragment, derivative, variant, or ortologue thereof.

The present invention further includes the nucleotide sequence as set forth in SEQ ID NO: 1, as well as portions of the genomic sequence, the cDNA sequence, allelic variants, synthetic variants and mutants thereof. This includes sequences that are to be used as probes, vectors for transformation or cloning intermediates.

SEQ ID NO. 2 is the deduced amino acid sequence from the open reading frame YJR098c in SEQ ID NO. 1.

Another aspect of the present invention relates to those polypeptides, which have at least 60% identity to SEQ ID NO: 2.

The invention furthermore relates to expression constructs for expressing yeast TEP in plants, preferably in plant seeds, transgenic plants expressing yeast TEP, and to the use of said transgenic plants for the production of food, feeds, seed, pharmaceuticals or fine chemical, in particular for the production of oils.

In oil crops like rape, sunflower, oil palm etc., the oil (i.e. triacylglycerols) is the most valuable product of the seeds or fruits and other compounds such as starch, protein and fiber is regarded as by-products with less value. Enhancing the quantity of oil per weight basis at the expense of other compounds in oil crops would therefore increase the value of the crop. If proteins that promote the allocation of reduced carbon into the production of oil can be up regulated by overexpression, the cells will accumulate more oil at the expense of other products. This approach could not only be used to increase the oil content in already high oil producing organisms such as oil crops, they could also lead to significant oil production in moderate or low oil containing crops such as soy, oat, maize, potato, sugar beats, and turnips as well as in microorganisms.

Increasing the oil content in plants and, in particular, in plant seeds is of great interest for traditional and modern plant breeding and in particular for plant biotechnology. Owing to the increasing consumption of vegetable oils for nutrition or industrial applications, possibilities of increasing or modifying vegetable oils are increasingly the subject of current research (for example Töpfer et al. (1995) Science 268:681-686). Its aim is in particular increasing the fatty acid content in seed oils.

The fatty acids which can be obtained from the vegetable oils are also of particular interest. They are employed, for example, as bases for plasticizers, lubricants, surfactants, cosmetics and the like and are employed as valuable bases in the food and feed industries. Thus, for example, it is of particular interest to provide rapeseed oils with fatty acids with medium chain length since these are in demand in particular in the production of surfactants.

The targeted modulation of plant metabolic pathways by recombinant methods allows the modification of the plant metabolism in an advantageous manner which, when using traditional breeding methods, could only be achieved after a complicated procedure or not at all. Thus, unusual fatty acids, for example specific poly-unsaturated fatty acids, are only synthesized in certain plants or not at all in plants and can therefore only be produced by expressing the relevant gene in transgenic plants (for example Millar et al. (2000) Trends Plant Sci 5:95-101).

Triacylgylcerides and other lipids are synthesized from fatty acids. Fatty acid biosynthesis and triacylglyceride biosynthesis can be considered as separate biosynthetic pathways owing to the compartmentalization, but as a single biosynthetic pathway in view of the end product. Lipid synthesis can be divided into two part-mechanisms, one which might be termed "prokaryotic" and another which may be termed "eukaryotic" (Browse et al. (1986) Biochemical J 235:25-31; Ohlrogge & Browse (1995) Plant Cell 7:957-970). The prokaryotic mechanism is localized in the plastids and encompasses the biosynthesis of the free fatty acids which are exported into the cytosol, where they enter the eukaryotic mechanism in the form of fatty acid acyl-CoA esters and are esterified with glycerol-3-phosphate (G3P) to give phosphatidic acid (PA). PA is the starting point for the synthesis of neutral and polar lipids. The neutral lipids are synthesized on the endoplasmic reticulum via the Kennedy pathway (Voelker (1996) Genetic Engineering, Setlow (ed.) 18:111-113; Shankline & Cahoon (1998) Annu Rev Plant Physiol Plant Mol Biol 49:611-649; Frentzen (1998) Lipids 100:161-166).

The last step in the synthesis of triacylglycerols has been shown to occur by two different enzymatic reactions, an acyl-CoA dependent reaction catalyzed by an acyl-CoA:diacylglycerol acyltransferase (Cases, et al., 1998; Lardizabal, et al., 2001) and the acyl-CoA independent reaction catalyzed by an phospholipid:diacylglyerol acyltransferase (Dahlqvist, et al., 2000). Two unrelated gene families encoding acyl-CoA:diacylglycerol acyltransferases have been identified in plants, animals and yeast, whereas the gene family encoding the acyl-CoA independent enzyme has been identified in yeast but not in plants or animals. In yeast, a total of four genes (are1, are2, lro1, dga1) belong to these three gene families, and they are the only genes known to contribute directly to triacylglycerol synthesis. Thus, no synthesis of triacylglycerol could be detected in yeast cells where all four genes were disrupted. In the present invention we show, that a fifth gene is present in yeast, which enhances the amount of triacylglycerol that accumulates in wildtype yeast.

It is an object of the present invention to provide alternative methods for increasing the oil content in plants.

We have found that this object is achieved by the present invention.

A first subject matter of the invention comprises a method of increasing the total oil content in a plant organism or a tissue, organ, part, cell or propagation material thereof, comprising a) the transgenic expression of yeast TEP in said plant organism or in a tissue, organ, part, cell or propagation material thereof, and b) the selection of plant organisms in which—in contrast to or comparison with the starting organism—the total oil content in said plant organism or in a tissue, organ, part, cell or propagation material thereof is increased.

Other proteins resulting in the same effect as the protein set forth in SEQ ID NO. 2 are obtainable from the specific sequences provided herein. Furthermore, it will be apparent that one can obtain natural and synthetic TEPs, including those with modified amino acid sequences and starting materials for synthetic-protein modeling from the exemplified TEPs and from TEPs which are obtained through the use of such exemplified sequences. Modified amino acid sequences include sequences that have been mutated, truncated, increased and the like, whether such sequences were partially or wholly synthesized.

Further, the nucleic acid probes (DNA or RNA) derived from the SEQ-ID No. 1 of the present invention can be used to screen and recover "homologous" or "related" sequences from a variety of plant and microbial sources.

The present invention can be essentially characterized by the following aspects:

Example 1 shows the reduction of triacylglycerol accumulation in yeast cells lacking the YJR098c gene.

Example 2 shows the increased accumulation of triacylglycerol in yeast cells expressing the YJR098c gene in combination with a strong promoter.

Example 3 shows a significantly higher total oil content in the seeds of transgenic plant lines with increased expression of the YJR098c gene construct.

Use of a nucleic acid sequence SEQ-ID No: 1, encoding a protein SEQ-ID No: 2 that enhances the production of triacylglycerol (TAG), by genetic transformation of an oil-producing organism with said sequence in order to be expressed in this organism, resulting in an active protein that increases the oil content of the organism. The nucleic acid sequence is derived from the sequence shown in SEQ ID NO. 1 from the *Saccharomyces cerevisiae* YJR098c gene (genomic clone or cDNA) or from a nucleic acid sequence or cDNA that contains a nucleotide sequence coding for a protein with an amino acid sequence that is 60% or more identical to the amino acid sequence as presented in SEQ ID No: 2.

The gene product, which we refer to as a TAG synthesis enhancing protein (TEP) is most likely not itself catalyzing the synthesis of TAG, but its presence elevates the amount of TAG synthesized by other enzymes.

The instant invention pertains to a gene construct comprising a said nucleotide sequence SEQ ID No: 1 of the instant invention, which is operably linked to a heterologous nucleic acid.

The term operably linked means a serial organization e.g. of a promoter, coding sequence, terminator and/or further regulatory elements whereby each element can fulfill its original function during expression of the nucleotide sequence.

Further, a vector comprising the said nucleotide sequence SEQ ID No: 1 of the instant invention is contemplated in the instant invention. This includes also an expression vector which can harbor a selectable marker gene and/or nucleotide sequences for the replication in a host cell and/or the integration into the genome of the host cell.

Furthermore, this invention relates to a method for producing a TEP in a host cell or progeny thereof including genetically engineered oil seeds, yeast and moulds or any other oil-accumulating organism, via the expression of a construct in the cell. Of particular interest is the expression of the nucleotide sequences of the present invention from transcription initiation regions that are preferentially expressed in plant seed tissues. It is further contemplated that an artificial gene sequence encoding TEP may be synthesized, especially to provide plant-preferred codons. Cells containing a TEP as a result of the production of a TEP encoding sequence are also contemplated within the scope of the invention.

Further, the invention pertains a transgenic cell or organism containing a said nucleotide sequence and/or a said gene construct and/or a said vector. The object of the instant invention is further a transgenic cell or organism which is an eucaryotic cell or organism. Preferably, the transgenic cell or organism is a yeast cell or a plant cell or a plant. The instant invention further pertains said transgenic cell or organism having an increased biosynthetic pathway for the production of substrates for the synthesis of triacylglycerol. A transgenic cell or organism having increased oil content is also contemplated within the scope of this invention.

Further, the invention pertains a transgenic cell or organism wherein the activity of TEP is increased in said cell or organism. The increased activity of TEP is characterized by an alteration in gene expression, catalytic activity and/or regulation of activity of the enzyme. Moreover, a transgenic cell or organism is included in the instant invention, wherein the increased biosynthetic pathway for the production of substrates for the production of triacylglycerol is characterized e.g. by the prevention of accumulation of undesirable fatty acids in the membrane lipids.

In a different embodiment, this invention also relates to methods of using a DNA sequence coding for a TEP for increasing the oil-content within the cells of different organisms.

Further, the invention makes possible a process for elevating the production of triacylglycerol, which comprises growing transgenic cells or organisms under conditions whereby the nucleotide sequence SEQ-ID No: 1 is expressed in order to produce an protein in these cells with the ability of enhancing the production of triacylglycerol.

Corresponding genes coding for TEP can be isolated from other organisms, especially yeast-type organisms, like e.g. *Schizosaccharomyces pombe, Yarrowia lipolytica, Zygosaccharomyces rouxii, Saccharomyces cerevisiae, Emericella nidulans* and *Debaryomyces hansenii*.

Transgenic organisms comprising, in their genome or on a plasmid, a nucleic acid sequence SEQ ID No:1 according to the above, transferred by recombinant DNA technology. One important type of transgenic organism covered by this invention are commercially relevant plants in which said nucleotide sequence preferably would be expressed under the control of a storage organ specific promoter. Alternatively, the nucleotide sequence could also be expressed under the control of a seed-specific promoter or any other promoter suitable for tissue-specific high-level expression in plants.

A protein encoded by a DNA molecule according to SEQ ID NO. 1 or a functional biologically active fragment thereof having TEP activity in transgenic organisms. Alternatively, the protein produced in an organism, which has the amino acid sequence set forth in SEQ ID NO. 2 or an amino acid sequence with at least 60% homology to said amino acid sequence having TEP activity. Preferably the protein is isolated from *Saccharomyces cerevisiae*.

Use of a protein according to SEQ ID No: 2 or derivatives of that protein having TEP activity for the increased production of triacylglycerols.

Surprisingly, it has been found that the heterologous expression of the yeast TEP from *Saccharomyces cerevisiae* SEQ ID NO: 1 in *Arabidopsis* leads to a significantly increased triacylglyceride (storage oils) content in the seeds. The oil content was increased by approximately 5%, in one transgenic line even by 10%, compared with wild-type control plants. The transgenic expression of the yeast TEP had no adverse effects on the growth or other properties of the transformed plants.

The method according to the invention can be applied in principle to all plant species, in addition to the species *Arabidopsis thaliana*, which is employed as model plant. The method according to the invention is preferably applied to oil crops whose oil content is already naturally high and/or for the industrial production of oils.

"Plant" organism or tissue, organ, part, cell or propagation material thereof is generally understood as meaning any single- or multi-celled organism or a cell, tissue, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. Also included are mature plants, seeds, shoots and seedlings, and parts, propagation material (for example tubors, seeds or fruits) and cultures derived from them, for example cell cultures or callus cultures.

"Plant" encompasses all annual and perennial monocotyledonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae, Umbelliferae.

Preferred monocotyledonous plants are selected in particular from the monocotyledonous crop plants such as, for example, the Gramineae family, such as rice, maize, wheat or other cereal species such as barley, millet and sorghum, rye, triticale or oats, and sugar cane, and all grass species.

The invention is applied very particularly preferably to dicotyledonous plant organisms. Preferred dicotyledonous plants are selected in particular from the dicotyledonous crop plants such as, for example, Asteraceae such as *Heliantus annuus* (sunflower), tagetes or *calendula* and others, Compositae, especially the genus *Lactuca*, very particularly the species *sativa* (lettuce) and others, Cruciferae, particularly the genus *Brassica*, very particularly the species *napus* (oilseed rape), *campestris* (beet), *oleracea* cv *Tastie* (cabbage), *oleracea* cv *Snowball* Y (cauliflower) and *oleracea* cv *Emperor* (broccoli) and other cabbages; and the genus *Arabidopsis*, very particularly the species *thaliana*, and cress or canola and others, Cucurbitaceae such as melon, pumpkin/squash or zucchini and others, Leguminosae, particularly the genus *Glycine*, very particularly the species *max* (soybean), soya, and alfalfa, pea, beans or peanut and others, Rubiaceae, preferably the subclass Lamiidae such as, for example *Coffea arabica* or *Coffea liberica* (coffee bush) and others, Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others, Sterculiaceae, preferably the subclass Dilleniidae such as, for example, *Theobroma cacao* (cacao bush) and others, Theaceae, preferably the subclass Dilleniidae such as, for example, *Camellia sinensis* or *Thea sinensis* (tea shrub) and others, Umbelliferae, particularly the genus *Daucus* (very particularly the species *carota* (carrot)) and *Apium* (very particularly the species *graveolens dulce* (celeary)) and others;

and linseed, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf plants which may be mentioned by way of example but not by limitation are angiosperms, bryophytes such as, for example, *Hepaticae* (liverworts) and *Musci* (mosses); pteridophytes such as ferns, horsetail and clubmosses; gymnosperms such as conifers, cycades, ginkgo and Gnetatae; algae such as Chlorophyceae, Phaeophpyceae, Rhodophyceae, Myxophyceae, Xanthophyceae, Bacillariophyceae (diatoms) and Euglenophyceae. Plants within the scope of the invention comprise by way of example and not by way of limitation, the families of the Rosaceae such as rose, Ericaceae such as rhododendron and azalea, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geranium, Liliaceae such as dracena, Moraceae such as ficus, Araceae such as cheeseplant and many others.

Furthermore, plant organisms for the purposes of the invention are further organisms capable of being photosynthetically active such as, for example, algae, cyanobacteria and mosses. Preferred algae are green algae such as, for example, algae from the genus *Haematococcus, Phaedactylum tricornatum, Volvox* or *Dunaliella*. *Synechocystis* is particularly preferred.

Most preferred are oil crops. Oil crops are understood as being plants whose oil content is already naturally high and/or which can be used for the industrial production of oils. These plants can have a high oil content and/or else a particular fatty acid composition which is of interest industrially. Preferred plants are those with a lipid content of at least 1% by weight. Oil crops encompassed by way of example: *Borvago officinalis* (borage); *Brassica* species such as *B. campestris, B. napus, B. rapa* (mustard, oilseed rape or turnip rape); *Cannabis sativa* (hemp); *Carthamus tinctorius* (safflower); *Cocos nucifera* (coconut); *Crambe abyssinica* (crambe); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirisutfum* (American cotton); *Gossypium barbadense* (Egyptian cotton); *Gossypium herbaceum* (Asian cotton); *Helianthus annuus* (sunflower); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Triticum* species (wheat); *Zea mays* (maize), and various nut species such as, for example, walnut or almond.

"Total oil content" refers to the sum of all oils, preferably to the sum of the triacylglycerides.

"Oils" encompasses neutral and/or polar lipids and mixtures of these. Those mentioned in Table 1 may be mentioned by way of example, but not by limitation.

TABLE 1

Classes of plant lipids

| | |
|---|---|
| Neutrale lipids | Triacylglycerol (TAG) |
| | Diacylglycerol (DAG) |
| | Monoacylglycerol (MAG) |
| Polar lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

Neutral lipids preferably refers to triacylglycerides. Both neutral and polar lipids may comprise a wide range of various fatty acids. The fatty acids mentioned in Table 2 may be mentioned by way of example, but not by limitation.

TABLE 2

Overview over various fatty acids (selection)

| Nomenclature[1] | Name |
|---|---|
| 16:0 | Palmitic acid |
| 16:1 | Palmitoleic acid |
| 16:3 | Roughanic acid |
| 18:0 | Stearic acid |
| 18:1 | Oleic acid |
| 18:2 | Linoleic acid |
| 18:3 | Linolenic acid |
| γ-18:3-18:3 | Gamma-linolenic acid* |
| 20:0 | Arachidic acid |
| 22:6 | Docosahexaenoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

[1]Chain length: number of double bonds
*not naturally occurring in plants

Oils preferably relates to seed oils.

"Increase in" the total oil content refers to the increased oil content in a plant or a part, tissue or organ thereof, preferably in the seed organs of the plants. In this context, the oil content is at least 5%, preferably at least 10%, particularly preferably at least 15%, very particularly preferably at least 20%, most preferably at least 25% increased under otherwise identical conditions in comparison with a starting plant which has not been subjected to the method according to the invention, but is otherwise unmodified. Conditions in this context means all of the conditions which are relevant for germination, culture or growth of the plant, such as soil conditions, climatic conditions, light conditions, fertilization, irrigation, plant protection treatment and the like.

"Yeast TEP" generally refers to all those proteins which are capable of increasing the oil content in oil producing organisms, especially microorganisms, yeast, fungi and plants and are identical to SEQ ID No: 2 or have homology to SEQ ID No: 2.

Yeast refers to the group of unicellular fungi with a pronounced cell wall and formation of pseudomycelium (in contrast to molds). They reproduce vegetatively by budding and/or fission (Schizo-*saccharomyces* and *Saccharomycodes*, respectively).

Encompassed are what are known as false yeasts, preferably the families Cryptococcaceae, Sporobolomycetaceae with the genera *Cryptococcus, Torulopsis, Pityrosporum, Brettanomyces, Candida, Kloeckera, Trigonopsis, Trichosporon, Rhodotorula* and *Sporobolomyces* and *Bullera*, and true yeasts (yeasts which also reproduce sexually; ascus), preferably the families endo- and saccharomycetaceae, with the genera *Saccharomyces, Debaromyces, Lipomyces, Hansenula, Endomycopsis, Pichia, Hanseniaspora*. Most preferred are the genera *Saccharomyces cerevisiae, Pichia pastoris, Hansenula polymorpha, Schizosaccharomyces pombe, Kluyveromyces lactis, Zygosaccharomyces rouxii,* and *Yarrowia lipolitica, Emericella nidulans, Aspergillus nidulans, Debaryomyces hansenii* and *Torulaspora hansenii*.

Yeast TEP refers in particular to the polypeptide sequence SEQ ID No: 2.

Most preferably, yeast TEP refers to the yeast protein TEP as shown in SEQ ID NO: 2 and functional equivalents or else functionally equivalent portions of the above.

Functional equivalents refers in particular to natural or artificial mutations of the yeast protein TEP as shown in SEQ ID NO: 2 and homologous polypeptides from other yeasts which have the same essential characteristics of a yeast TEP as defined above. Mutations encompass substitutions, additions, deletions, inversions or insertions of one or more amino acid residues.

The yeast TEP to be employed advantageously within the scope of the present invention can be found readily by database searches or by screening gene or cDNA libraries using the yeast TEP sequence shown in SEQ ID NO: 2, which is given by way of example, or the nucleic acid sequence as shown in SEQ ID NO: 1, which encodes the latter, as search sequence or probe.

Said functional equivalents preferably have at least 60%, particularly preferably at least 70%, particularly preferably at least 80%, most preferably at least 90% homology with the protein of SEQ ID NO: 2.

Homology between two polypeptides is understood as meaning the identity of the amino acid sequence over the entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap Weight: 8 | Length Weight: 2 |
| Average Match: 2,912 | Average Mismatch: −2,003 |

For example, a sequence with at least 80% homology with the sequence SEQ ID NO: 2 at the protein level is understood as meaning a sequence which, upon comparison with the sequence SEQ ID NO: 2 with the above program algorithm and the above parameter set has at least 80% homology.

Functional equivalents also encompass those proteins which are encoded by nucleic acid sequences which have at least 60%, particularly preferably at least 70%, particularly preferably at least 80%, most preferably at least 90% homology with the nucleic acid sequence with the SEQ ID NO: 1.

Homology between two nucleic acid sequences is understood as meaning the identity of the two nucleic acid sequences over the entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap Weight: 50 | Length Weight: 3 |
| Average Match: 10 | Average Mismatch: 0 |

For example, a sequence which has at least 80% homology with the sequence SEQ ID NO: 1 at the nucleic acid level is understood as meaning a sequence which, upon comparison with the sequence SEQ ID NO: 1 within the above program algorithm with the above parameter set has a homology of at least 80%.

Functional equivalents also encompass those proteins which are encoded by nucleic acid sequences which hybridize under standard conditions with a nucleic acid sequence described by SEQ ID NO: 1, the nucleic acid sequence which is complementary thereto or parts of the above and which have the essential characteristics for a yeast TEP.

"Standard hybridization conditions" is to be understood in the broad sense, but preferably refers to stringent hybridization conditions. Such hybridization conditions are described, for example, by Sambrook J, Fritsch E F, Maniatis T et al., in Molecular Cloning (A Laboratory Manual), 2$^{nd}$ edition, Cold Spring Harbor Laboratory Press, 1989, pages 9.31-9.57) or in Current Protocols in Molecular Biology, John Wiley & Sons, N.Y. (1989), 6.3.1-6.3.6. For example, the conditions during the wash step can be selected from the range of high-stringency conditions (with approximately 0.2×SSC at 50° C., preferably at 65° C.) (20×SSC: 0.3 M sodium citrate, 3 M NaCl, pH 7.0). Denaturing agents such as, for example, formamide or SDS may also be employed during hybridization. In the presence of 50% formamide, hybridization is preferably carried out at 42° C.

The invention furthermore relates to transgenic expression constructs which can ensure a transgenic expression of a yeast TEP in a plant organism or a tissue, organ, part, cells or propagation material of said plant organism.

The definition given above applies to yeast TEP, with the transgenic expression of a yeast TEP described by the sequence with the SEQ ID NO: 2 being particularly preferred.

In said transgenic expression constructs, a nucleic acid molecule encoding a yeast TEP is preferably in operable linkage with at least one genetic control element (for example a promoter) which ensures expression in a plant organism or a tissue, organ, part, cell or propagation material of same.

Especially preferred are transgenic expression cassettes wherein the nucleic acid sequence encoding a TEP is described by a) a sequence with the SEQ ID NO: 1,
b) a sequence derived from a sequence with the SEQ ID NO: 1 in accordance with the degeneracy of the genetic code
c) a sequence which has at least 60% identity with the sequence with the SEQ ID NO: 1.

Operable linkage is understood as meaning, for example, the sequential arrangement of a promoter with the nucleic acid sequence encoding a yeast TEP which is to be expressed (for example the sequence as shown in SEQ ID NO: 1 and, if appropriate, further regulatory elements such as, for example, a terminator in such a way that each of the regulatory elements can fulfil its function when the nucleic acid sequence is expressed recombinantly. Direct linkage in the chemical sense is not necessarily required for this purpose. Genetic control sequences such as, for example, enhancer sequences can also exert their function on the target/sequence from positions which are further removed or indeed from other DNA molecules. Preferred arrangements are those in which the nucleic acid sequence to be expressed recombinantly is positioned behind the sequence acting as promoter so that the two sequences are linked covalently to each other. The distance between the promoter sequence and the nucleic acid sequence to be expressed recombinantly is preferably less than 200 base pairs, particularly preferably less than 100 base pairs, very particularly preferably less than 50 base pairs.

Operable linkage and a transgenic expression cassette can both be effected by means of conventional recombination and cloning techniques as they are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L und Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or of a signal peptide, may also be positioned between the two sequences. Also, the insertion of sequences may lead to the expression of fusion proteins. Preferably, the expression cassette composed of a promoter linked to a nucleic acid sequence to be expressed can be in a vector-integrated form and can be inserted into a plant genome, for example by transformation.

However, a transgenic expression cassette is also understood as meaning those constructs where the nucleic acid sequence encoding a yeast TEP is placed behind an endogenous plant promoter in such a way that the latter brings about the expression of the yeast TEP.

Promoters which are preferably introduced into the transgenic expression cassettes are those which are operable in a plant organism or a tissue, organ, part, cell or propagation material of same. Promoters which are operable in plant organisms is understood as meaning any promoter which is capable of governing the expression of genes, in particular foreign genes, in plants or plant parts, plant cells, plant tissues or plant cultures. In this context, expression may be, for example, constitutive, inducible or development-dependent.

The following are preferred:

a) Constitutive promoters

"Constitutive" promoters refers to those promoters which ensure expression in a large number of, preferably all, tissues over a substantial period of plant development, preferably at all times during plant development (Benfey et al. (1989) EMBO J 8:2195-2202). A plant promoter or promoter originating from a plant virus is especially preferably used. The promoter of the CaMV (cauliflower mosaic virus) 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202) are especially preferred. Another suitable constitutive promoter is the Rubisco small subunit (SSU) promoter (U.S. Pat. No. 4,962,028), the leguminB promoter (GenBank Acc. No. X03677), the promoter of the nopalin synthase from *Agrobacterium*, the TR dual promoter, the OCS (octopine synthase) promoter from Agrobacterium, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits, the promoter of the

*Arabidopsis thaliana* nitrilase-1 gene (GenBank Acc. No.: U38846, nucleotides 3862 to 5325 or else 5342) or the promoter of a proline-rich protein from wheat (WO 91/13991), and further promoters of genes whose constitutive expression in plants is known to the skilled worker. The CaMV 35S promoter and the *Arabidopsis thaliana* nitrilase-1 promoter are particularly preferred.

b) Tissue-Specific Promoters

Furthermore preferred are promoters with specificities for seeds, such as, for example, the phaseolin promoter (U.S. Pat. No. 5,504,200; Bustos M M et al. (1989) Plant Cell 1(9):839-53), the promoter of the 2S albumin gene (Joseffson L G et al. (1987) J Biol Chem 262:12196-12201), the legumine promoter (Shirsat A et al. (1989) Mol Gen Genet 215(2):326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the promoter of the sucrose binding proteins (WO 00/26388) or the legumin B4 promoter (LeB4; Bäumlein H et al. (1991) Mol Gen Genet 225: 121-128; Bäumlein et al. (1992) Plant Journal 2(2):233-9; Fiedler U et al. (1995) Biotechnology (NY) 13(10):1090f), the *Arabidopsis* oleosin promoter (WO 98/45461), and the *Brassica* Bce4 promoter (WO 91/13980).

Further suitable seed-specific promoters are those of the gene encoding high-molecular weight glutenin (HMG), gliadin, branching enyzme, ADP glucose pyrophosphatase (AG-Pase) or starch synthase. Promoters which are furthermore preferred are those which permit a seed-specific expression in monocots such as maize, barley, wheat, rye, rice and the like. The promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the casirin gene or the secalin gene) can advantageously be employed.

c) Chemically Inducible Promoters

The expression cassettes may also contain a chemically inducible promoter (review article: Gatz et al. (1997) Annu Rev Plant Physiol Plant Mol Biol 48:89-108), by means of which the expression of the exogenous gene in the plant can be controlled at a particular point in time. Such promoters such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1992) Plant J 2:397-404), an abscisic acid-inducible promoter EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots.

Particularly preferred are constitutive promoters, very particularly preferred seed-specific promoters, in particular the napin promoter and the USP promoter.

In addition, further promoters which make possible expression in further plant tissues or in other organisms such as, for example, *E. coli* bacteria, may be linked operably with the nucleic acid sequence to be expressed. Suitable plant promoters are, in principle, all of the above-described promoters.

The nucleic acid sequences present in the transgenic expression cassettes according to the invention or transgenic vectors can be linked operably with further genetic control sequences besides a promoter. The term genetic control sequences is to be understood in the broad sense and refers to all those sequences which have an effect on the establishment or the function of the expression cassette according to the invention. Genetic control sequences modify, for example, transcription and translation in prokaryotic or eukaryotic organisms. The transgenic expression cassettes according to the invention preferably encompass a plant-specific promoter 5'-upstream of the nucleic acid sequence to be expressed recombinantly in each case and, as additional genetic control sequence, a terminator sequence 3'-downstream, and, if appropriate, further customary regulatory elements, in each case linked operably with the nucleic acid sequence to be expressed recombinantly.

Genetic control sequences also encompass further promoters, promoter elements or minimal promoters capable of modifying the expression-controlling properties. Thus, genetic control sequences can, for example, bring about tissue-specific expression which is additionally dependent on certain stress factors. Such elements are, for example, described for water stress, abscisic acid (Lam E and Chua N H, J Biol Chem 1991; 266(26): 17131-17135) and thermal stress (Schoffl F et al. (1989) Mol Gen Genetics 217(2-3): 246-53).

Further advantageous control sequences are, for example, in the Gram-positive promoters amy and SPO2, and in the yeast or fungal promotors ADC1, MFa, AC, P-60, CYC1, GAPDH, TEF, rp28, ADH.

In principle all natural promoters with their regulatory sequences like those mentioned above may be used for the method according to the invention. In addition, synthetic promoters may also be used advantageously.

Genetic control sequences further also encompass the 5'-untranslated regions, introns or nonencoding 3'-region of genes, such as, for example, the actin-1 intron, or the Adh1-S intron 1, 2 and 6 (for general reference, see: The Maize Handbook, Chapter 116, Freeling and Walbot, Eds., Springer, New York (1994)). It has been demonstrated that these may play a significant role in regulating gene expression. Thus, it has been demonstrated that 5'-untranslated sequences can enhance the transient expression of heterologous genes. Translation enhancers which may be mentioned by way of example are the tobacco mosaic virus 5' leader sequence (Gallie et al. (1987) Nucl Acids Res 15:8693-8711) and the like. They may furthermore promote tissue specificity (Rouster J et al. (1998) Plant J 15:435-440).

The transient expression cassette can advantageously contain one or more of what are known as enhancer sequences in operable linkage with the promoter, and these make possible an increased recombinant expression of the nucleic acid sequence. Additional advantageous sequences such as further regulatory elements or terminators may also be inserted at the 3' end of the nucleic acid sequences to be expressed recombinantly. One or more copies of the nucleic acid sequences to be expressed recombinanly may be present in the gene construct.

Polyadenylation signals which are suitable as control sequences are plant polyadenylation signals, preferably those which correspond essentially to *Agrobacterium tumefaciens* T-DNA polyadenylation signals, in particular those of gene 3 of the T-DNA (octopine synthase) of the Ti plasmid pTiACHS (Gielen et al. (1984) EMBO J 3:835 et seq.) or functional equivalents thereof. Examples of particularly suitable terminator sequences are the OCS (octopin synthase) terminator and the NOS (nopaline synthase) terminator.

Control sequences are furthermore understood as those which make possible homologous recombination or insertion into the genome of a host organism, or removal from the genome. In the case of homologous recombination, for example, the coding sequence of the specific endogenous gene can be exchanged in a directed fashion for a sequence encoding a dsRNA. Methods such as the cre/lox technology permit the tissue-specific, possibly inducible, removal of the expression cassette from the genome of the host organism (Sauer B (1998) Methods. 14(4):381-92). Here, certain flanking sequences are added to the target gene (lox sequences), and these make possible removal by means of cre recombinase at a later point in time.

A recombinant expression cassette and the recombinant vectors derived from it may comprise further functional elements. The term functional element is to be understood in the broad sense and refers to all those elements which have an effect on generation, replication or function of the expression cassettes vectors or transgenic organisms according to the invention. Examples which may be mentioned, but not by way of limitation, are:

a) Selection markers which confer resistance to a metabolism inhibitor such as 2-deoxyglucose-6-phosphate (WO 98/45456), antibiotics or biocides, preferably herbicides, such as, for example, kanamycin, G 418, bleomycin, hygromycin, or phosph nothricin and the like. Particularly preferred selection markers are those which confer resistance to herbicides. The following may be mentioned by way of example: DNA sequences which encode phosphinothricin acetyltransferases (PAT) and which inactivate glutamine synthase inhibitors (bar and pat gene), 5-enolpyruvylshikimate-3-phosphate synthase genes (EPSP synthase genes), which confer resistance to Glyphosate (N-(phosphonomethyl)glycine), the gox gene, which encodes Glyphosate-degrading enzyme (Glyphosate oxidoreductase), the deh gene (encoding a dehalogenase which inactivates dalapon), sulfonylurea- and imidazolinone-inactivating acetolactate synthases, and bxn genes which encode nitrilase enzymes which degrade bromoxynil, the aasa gene, which confers resistance to the antibiotic apectinomycin, the streptomycin phosphotransferase (SPT) gene, which permits resistance to streptomycin, the neomycin phosphotransferase (NPTII) gene, which confers resistance to kanamycin or geneticidin, the hygromycin phosphotransferase (HPT) gene, which confers resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and which allow the transformation efficacy or the expression site or time to be assessed via their color or enzyme activity. Very particularly preferred in this context are reporter proteins (Schenborn E, Groskreutz D. Mol Biotechnol. 1999; 13(1):29-44) such as the "green fluorescent protein" (GFP) (Sheen et al. (1995) Plant Journal 8(5):777-784), chloramphenicol transferase, a luciferase (Ow et al. (1986) Science 234:856-859), the aequorin gene (Prasher et al. (1985) Biochem Biophys Res Commun 126(3):1259-1268), β-galactosidase, with β-glucuronidase being very particularly preferred (Jefferson et al. (1987) EMBO J 6:3901-3907).

c) Replication origins which allow replication of the expression cassettes or vectors according to the invention in, for example, E. coli. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are required for agrobacterium-mediated plant transformation such as, for example, the right or left border of the T-DNA, or the vir region.

To select cells which have successfully undergone homologous recombination or else cells which have succesfully been transformed, it is generally required additionally to introduce a selectable marker which confers resistance to a biocide (for example a herbicide), a metabolism inhibitor such as 2-deoxyglucose-6-phosphate (WO 98/45456) or an antibiotic to the cells which have successfully undergone recombination. The selection marker permits the selection of the transformed cells from untransformed cells (McCormick et al. (1986) Plant Cell Reports 5:81-84).

In addition, said recombinant expression cassette or vectors may comprise further nucleic acid sequences which do not encode a yeast TEP and whose recombinant expression leads to a further increase in fatty acid biosynthesis. By way of example, but not by limitation, such a proOIL nucleic acid sequence which is additionally expressed recombinantly can be selected from among nucleic acids encoding acetyl-CoA carboxylase (ACCase), glycerol-3-phosphate acyltransferase (GPAT), lysophosphatidate acyltransferase (LPAT), diacylglycerol acyltransferase (DAGAT) and phospholipid:diacylglycerol acyltransferase (PDAT). Such sequences are known to the skilled worker and are readily accessible from databases or suitable cDNA libraries of the respective plants.

An expression cassette according to the invention can advantageously be introduced into an organism or cells, tissues, organs, parts or seeds thereof (preferably into plants or plant cells, tissues, organs, parts or seeds) by using vectors in which the recombinant expression cassettes are present. The invention therefore furthermore relates to said recombinant vectors which encompass a recombinant expression cassette for a yeast TEP.

For example, vectors may be plasmids, cosmids, phages, viruses or else agrobacteria. The expression cassette can be introduced into the vector (preferably a plasmid vector) via a suitable restriction cleavage site. The resulting vector is first introduced into E. coli. Correctly transformed E. coli are selected, grown, and the recombinant vector is obtained with methods known to the skilled worker. Restriction analysis and sequencing may be used for verifying the cloning step. Preferred vectors are those which make possible stable integration of the expression cassette into the host genome.

The invention furthermore relates to transgenic plant organisms or tissues, organs, parts, cells or propagation material thereof which comprise a yeast TEP as defined above, a transgenic expression cassette for a yeast TEP or a transgenic vector encompassing such an expression cassette.

Such a transgenic plant organism is generated, for example, by means of transformation or transfection of the corresponding proteins or nucleic acids. The generation of a transformed organism (or a transformed cell or tissue) requires introducing the DNA in question (for example the expression vector), RNA or protein into the host cell in question. A multiplicity of methods is available for this procedure, which is termed transformation (or transduction or transfection) (Keown et al. (1990) Methods in Enzymology 185:527-537). Thus, the DNA or RNA can be introduced for example directly by microinjection or by bombardment with DNA-coated microparticles. The cell may also be permeabilized chemically, for example with polyethylene glycol, so that the DNA may reach the cell by diffusion. The DNA can also be introduced by protoplast fusion with other DNA-comprising units such as minicells, cells, lysosomes or liposomes. Electroporation is a further suitable method for introducing DNA; here, the cells are permeabilized reversibly by an electrical pulse. Soaking plant parts in DNA solutions, and pollen or pollen tube transformation, are also possible. Such methods have been described (for example in Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208: 1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the methods which have been described for transforming and regenerating plants from plant tissues or plant cells are exploited for transient or stable transformation. Suitable methods are, in particular, protoplast transformation by polyethylene glycol-induced DNA uptake, the biolistic method with the gene gun, what is known as the particle bombardment method, electroporation, the incubation of dry embryos in DNA-containing solution, and microinjection.

In addition to these "direct" transformation techniques, transformation may also be effected by bacterial infection by means of *Agrobacterium tumefaciens* or *Agrobacterium rhizogenes* and the transfer of corresponding recombinant Ti plasmids or Ri plasmids by infection with transgenic plant viruses. *Agrobacterium*-mediated transformation is best suited to cells of dicotyledonous plants. The methods are described, for example, in Horsch R B et al. (1985) Science 225: 1229f).

When agrobacteria are used, the expression cassette is to be integrated into specific plasmids, either into a shuttle vector or into a binary vector. If a Ti or Ri plasmid is to be used for the transformation, at least the right border, but in most cases the right and left border, of the Ti or Ri plasmid T-DNA is linked to the expression cassette to be introduced as flanking region.

Binary vectors are preferably used. Binary vectors are capable of replication both in *E. coli* and in *Agrobacterium*. As a rule, they contain a selection marker gene and a linker or polylinker flanked by the right and left T-DNA border sequence. They can be transformed directly into *Agrobacterium* (Holsters et al. (1978) Mol Gen Genet 163:181-187). The selection marker gene, which is, for example, the nptII gene, which confers resistance to kanamycin, permits a selection of transformed agrobacteria. The Agrobacterium which acts as host organism in this case should already contain a plasmid with the vir region. The latter is required for transferring the T-DNA to the plant cells. An *Agrobacterium* transformed in this way can be used for transforming plant cells. The use of T-DNA for the transformation of plant cells has been studied intensively and described (EP 120 516; Hoekema, In: The Binary Plant Vector System, Offsetdrukkerij Kanters B. V., Alblasserdam, Chapter V; An et al. (1985) EMBO J 4:277-287). Various binary vectors, some of which are commercially available, such as, for example, pBI101.2 or pBIN19 (Clontech Laboratories, Inc. USA), are known.

Further promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type. In cases where DNA or RNA are injected or electroporated into plant cells, the plasmid used need not meet any particular requirements. Simple plasmids such as those from the pUC series may be used. If intact plants are to be regenerated from the transformed cells, it is necessary for an additional selectable marker gene to be present on the plasmid.

Stably transformed cells, i.e. those which contain the inserted DNA integrated into the DNA of the host cell, can be selected from untransformed cells when a selectable marker is part of the inserted DNA. By way of example, any gene which is capable of conferring resistance to antibiotics or herbicides (such as kanamycin, G 418, bleomycin, hygromycin or phosphinothricin and the like) is capable of acting as marker (see above). Transformed cells which express such a marker gene are capable of surviving in the presence of concentrations of such an antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide Glyphosate. The selection marker permits selection of transformed cells from untransformed cells (McCormick et al. (1986) Plant Cell Reports 5:81-84). The plants obtained can be bred and hybridized in the customary manner. Two or more generations should be grown in order to ensure that the genomic integration is stable and hereditary.

The above-described methods are described, for example, in Jenes B et al. (1993) Techniques for Gene Transfer, in: Transgenic Plants, Vol. 1, Engineering and Utilization, edited by SD Kung and R Wu, Academic Press, pp. 128-143, and in Potrykus (1991) Annu Rev Plant Physiol Plant Molec Biol 42:205-225). The construct to be expressed is preferably cloned into a vector which is suitable for transforming *Agrobacterium tumefaciens*, for example pBin19 (Bevan et al. (1984) Nucl Acids Res 12:8711f).

Once a transformed plant cell has been generated, an intact plant can be obtained using methods known to the skilled worker. For example, callus cultures are used as starting material. The development of shoot and root can be induced in this as yet undifferentiated cell biomass in the known fashion. The plantlets obtained can be planted out and used for breeding.

The skilled worker is familiar with such methods for regenerating plant parts and intact plants from plant cells. Methods which can be used for this purpose are, for example, those described by Fennell et al. (1992) Plant Cell Rep. 11: 567-570; Stoeger et al (1995) Plant Cell Rep. 14:273-278; Jahne et al. (1994) Theor Appl Genet 89:525-533.

"Transgenic", for example in the case of a yeast TEP, refers to a nucleic acid sequence, an expression cassette or a vector comprising said TEP nucleic acid sequence or to an organism transformed with said nucleic acid sequence, expression cassette or vector or all those constructs established by recombinant methods in which either a) the nucleic acid sequence encoding a yeast TEP or
b) a genetic control sequence, for example a promoter which is functional in plant organisms, which is linked operably with said nucleic acid sequence under a)
c) (a) or (b)

are not in their natural genetic environment or have been modified by recombinant methods, it being possible for the modification to be, for example, a substitution, addition, deletion, inversion or insertion of one or more nucleotide residues. Natural genetic environment refers to the natural chromosomal locus in the source organism or the presence in a genomic library. In the case of a genomic library, the natural genetic environment of the nucleic acid sequence is preferably retained, at least to some extent. The environment flanks the nucleic acid sequence at least on one side and has a sequence length of at least 50 bp, preferably at least 500 bp, particularly preferably at least 1000 bp, very particularly preferably at least 5000 bp. A naturally occurring expression cassette, for example the naturally occurring combination of the promoter of a gene encoding for a yeast TEP with the corresponding yeast TEP gene, becomes a transgenic expression cassette when the latter is modified by non-natural, synthetic ("artificial") methods such as, for example, a mutagenization. Such methods are described (U.S. Pat. No. 5,565,350; WO 00/15815; see also above).

Host or starting organisms which are preferred as transgenic organisms are, above all, plants in accordance with the above definition. Included for the purposes of the invention are all genera and species of higher and lower plants of the Plant Kingdom, in particular plants which are used for obtaining oils, such as, for example, oilseed rape, sunflower, sesame, safflower, olive tree, soya, maize, wheat and nut species. Furthermore included are the mature plants, seed, shoots and seedlings, and parts, propagation material and cultures, for example cell cultures, derived therefrom. Mature plants refers to plants at any desired developmental stage beyond the seedling stage. Seedling refers to a young, immature plant at an early developmental stage.

The transgenic organisms can be generated with the above-described methods for the transformation or transfection of organisms.

The invention furthermore relates to the use of the transgenic organisms according to the invention and to the cells, cell cultures, parts—such as, for example, in the case of transgenic plant organisms roots, leaves and the like—and transgenic propagation material such as seeds or fruits which are derived therefrom for the production of foodstuffs or feedstuffs, pharmaceuticals or fine chemicals, in particular oils, fats, fatty acids or derivatives of these.

Besides influencing the oil content, the transgenic expression of a yeast TEP SEQ ID No: 1 or derivatives thereof in plants may mediate yet further advantageous effects such as, for example, an increased stress resistance. Such osmotic stress occurs for example in saline soils and water and is an increasing problem in agriculture. Increased stress tolerance makes it possible, for example, to use areas in which conventional arable plants are not capable of thriving for agricultural usage.

The invention now having been generally described will be more readily understood by reference to the following examples, which are included for the purpose of illustration only, and are not intended to limit scope of the present invention.

EXAMPLES

General Methods:

Unless otherwise specified, all chemicals were from Fluka (Buchs), Merck (Darmstadt), Roth (Karlsruhe), Serva (Heidelberg) and Sigma (Deisenhofen). Restriction enzymes, DNA-modifying enzymes and molecular biological kits were from Amersham-Pharmacia (Freiburg), Biometra (Göttingen), Roche (Mannheim), New England Biolabs (Schwalbach), Novagen (Madison, Wis., USA), Perkin-Elmer (Weiterstadt), Qiagen (Hilden), Stratagen (Amsterdam, Netherlands), Invitrogen (Karlsruhe) and Ambion (Cambridgeshire, United Kingdom). The reagents used were employed in accordance with the manufacturer's instructions.

For example, oligonucleotides can be synthesized chemically in the known manner using the phosphoamidite method (Voet, Voet, $2^{nd}$ edition, Wiley Press New York, pages 896-897). The cloning steps carried out for the purposes of the present invention such as, for example, restriction cleavages, agarose gel electrophoreses, purification of DNA fragments, transfer of nucleic acids to nitrocellulose and nylon membranes, linking DNA fragments, transformation of E. coli cells, bacterial cultures, multiplication of phages and sequence analysis of recombinant DNA, are carried out as decribed by Sambrook et al. (1989) Cold Spring Harbor Laboratory Press; ISBN 0-87969-309-6. Recombinant DNA molecules were sequenced using an ABI laser fluorescence DNA sequencer following the method of Sanger (Sanger et al. (1977) Proc Natl Acad Sci USA 74:5463-5467).

Example 1

Reduction of Triacylglycerol Accumulation in Yeast Cells Lacking the YJR098c Gene Yeast strains used in this study were congenic to the W303-1A (Thomas & Rothstein, 1989) background. An YJR098c mutant strain, H1223, with the genotype MATα yjr098c::HIS3 ADE2 can 1-100 his3-11, 15 leu2-3, 112, trp1-1 ura3-1, was generated as described in Sandager et al., 2002. As a wild type control, we used the strain SCY62 MATa ADE2 can 1-100 his3-11,15 leu2-3, 112 trp1-1 ura3-1).

Yeast cells were cultivated at 30° C. on a rotary shaker in liquid synthetic medium (Sherman et al., 1986) supplemented with 2% (wt/vol) glucose.

The lipid content of the yeast cells was determined as described by Dahlqvist et al. (2000) and is presented as nmol of fatty acid (FA) per mg dry weight yeast.

The lipid content of a mutant yeast strain H1223, in which the YJR098c gene was disrupted, was analyzed and compared to wild type yeast cells (strain SCY62). The lipid content was determined in yeast cells harvested in stationary phase after 50 hours of cultivation in liquid synthetic medium at 30° C. Lipids were extracted in chloroform, fractionated on TLC and quantified by GC analyses (Dahlqvist et al., 2000). The total lipid content, measured as nmol fatty acids (FA) per dry weight yeast, in the YJR098c mutant yeast was 18% less than in the wild type, see table 1. The main reason for this difference was a lowered TAG content in the YJR098c mutant. Thus, the triacylglycerol amount in the mutant yeast was almost 36% lower than in the wild type, whereas the polar lipid content only differed slightly between the YJR098 mutant and the wild type yeast, see table 1.

In summary, this experiment shows that the product of the YJR098c gene contributes to TAG accumulation in yeast.

TABLE 1

Lipid content in yeast disrupted in the YJR098c gene.

|  | control yeast (nmol FA/mg) | YJR098c - mutant (nmol FA/mg) |
|---|---|---|
| Sterol esters | 28 | 25 |
| Triacylglycerol | 180 | 116 |
| Other neutral lipids | 7 | 9 |
| Polar lipids | 95 | 104 |
| Total lipids | 311 | 255 |

Example 2

Increased Accumulation of Triacylglycerol in Yeast Cells Expressing the YJR098c Gene in Combination with a Strong Promoter For induced high level expression of the YJR098c gene, a 2439 bp DNA fragment, containing 29 bp up stream and 442 bp down stream of the gene, was amplified from wt W303 genomic DNA by using a 1:1 mixture of Taq and pfu DNA polymerases with the 5' primer, CTTGTAGAGGT-TAACTGGGGA, and the 3' primer, TGAATTGTC-CTCGCTGTCAA. The resulting PCR product was blunt end cloned into the BamHI site of the GAL1 yeast expression plasmid pUS10, which is a selection marker variant of the GAL1 yeast expression plasmid pJN92 (Ronne et al., 1991) thus generating the plasmid pUS30. PUS 10 was generated by removing the URA3 selection marker from the pJN92 plasmid by HindIII digestion and replacing it with the HIS3 gene, a 1768 bp DNA fragment that was blunt end cloned into the remaining part of the HINDIII digested pJN92. The wild type yeast strain SCY62 (MATa ADE2 can 1-100 his3-11,15 leu2-3, 112 trp1-1 ura3-1), was transformed with the pUS30 and cultivated at 28° C. on a rotary shaker in synthetic medium (Sherman et al., 1986) lacking uracil and supplemented with 2% (vol/vol) glycerol and 2% (vol/vol) ethanol. The GAL1 promoter was induced after 6 or 24 hours of growth by the addition of 2% (wt/vol) final concentration of galactose. Cells were harvested after an additional 24 hours of growth. Wild type cells SCY62 (MATa ADE2 can 1-100 his3-11,15 leu2-3, 112 trp1-1 ura3-1) transformed with the empty vector, pUS10, and cultivated under identical conditions were used as a control. The lipid content of the yeast cells was determined as described by Dahlqvist et al. (2000) and is presented as nmol of fatty acid (FA) per mg dry weight yeast.

The effect of high-level expression of the YJR098c gene on lipid accumulation was studied by transforming the wild-type yeast strain SCY62 (Dahlqvist, et al., 2000) with a plasmid containing the YJR098c gene under control of the galactose-induced GALL promoter, see Table 2. High-level expression of the YJR098c gene from this promoter had no strong effect on the growth rate as determined by optical density measurements. The expression of the YJR098c gene was induced after 6 h (Table 2A) or 24 h (Table 2B) and cells were harvested after an additional 24 hours of cultivation. The total lipid content, determined as nmol fatty acids (FA) per mg yeast (Dahlqvist et al., 2000) in cells expressing the YJR098c gene from the GAL1 promoter was higher both at an early (Table 2A) or late (Table 2B) stationary growth stage as compared to cells transformed with an empty vector.

The elevated lipid content in cells expressing the YJR098c gene from the GAL1 promoter was entirely explained by an increased TAG content whereas the content of polar lipids and sterol esters were unaffected.

In summary, the TAG content in yeast cells expressing YJR098c in combination with a strong promoter was increased with 26 to 28% as compared to the control (Table 2A and 2 B), which demonstrates the potential of the use of the YJR098c gene for increasing the oil content in transgenic organisms including yeast.

TABLE 2

Lipid content in yeast that expresses the YJR098c gene in combination with the GAL1 promoter

|  | control yeast (nmol FA/mg) | High level of YJR098c expression (nmol FA/mg) |
| --- | --- | --- |
| A |  |  |
| Sterol esters | 13 | 13 |
| Triacylglycerol | 78 | 98 |
| Other neutral lipids | 9 | 9 |
| Polar lipids | 60 | 60 |
| Total lipids | 160 | 180 |
| B |  |  |
| Sterol esters | 15 | 17 |
| Triacylglycerol | 142 | 182 |
| Other neutral lipids | 9 | 11 |
| Polar lipids | 55 | 50 |
| Total lipids | 221 | 260 |

Example 3

Transgenic Plants Expressing YJR098c

For induced high level expression of the YJR098c gene in plants, a PCR fragment (2409 bp) was generated by the 5' primer (CTT GTA GAG GTT AAC TGG GGA) and the 3'primer (TGA ATT GTC CTC GCT GTC AA) adding 29 bases upstream of the gene and 442 bases downstream of the gene. The gene was cloned into the SmaI site of the vector pUC119 thus generating pUS 29. For Agrobacterium-mediated plant transformation a binary vector system including the primary cloning vector pART7 with a CaMV35S promoter and a binary pART27 vector (Gleave A., 1992) were used. The pART7 vector with a napin promoter is a construct where the napin promoter fragment (1101 bp) described by Stalberg (1993) replaced the CaMV35S promoter from pART7 only loosing the XhoI site of the polylinker in the process. The YJR098c fragment were cut out from pUS 29 at the XbaI and SacI site and then blunted into the pART7 vector with either the CaMV35S promoter, generating pEW 17 or with the napin promoter, generating pEW 14. The entire cartridge including the promoter, the YJR098c gene and a transcriptional termination region were removed from the pART7 vector as a NotI fragment and introduced directly to the pART27 vector. The plasmid was transformed into Agrobacterium tumefaciens.

Using floral dip essentially as described by Clough and Bent, 1998, plants of Arabidopsis thaliana were transformed with Agrobacterium tumefaciens GV3101 harboring either of the plasmids pEWART27-14 and pEWART27-17. Entire plants (inflorescence and rosette) were submerged for 20 to 30 sec in the infiltration media consisting of 5% sucrose and 0.02% Silwet L-77 (Osi Specialties, Danbury, Conn.) plus resuspended transformed A. tumefaciens cells. Plants were then transferred to a growth chamber with a photoperiod of 16 h of light at 21° C. and 8 h of dark at 18° C. (70% humidity).

The seed oil content of T2 plants of the Arabidopsis transformants was analyzed by the use of conventional gas-liquid chromatography (GLC). As controls, seeds from wild type plants were used. The level of expression of the YJR098c gene in the seeds is determined by Northern blot analysis.

The result of the measurements for the lines comprising the YJR098c construct showed a significantly higher total oil content in transgenic lines compared to the measurements of wild-type plants.

REFERENCES

Cases, S., Smith, S. J., Zheng, Y-W., Myers, H. M., Lear, S. R., Sande E., Novak, S., Collins, C., Welch, C. B., Lusis, A. J., Erickson, S. K., and Farese, R. V. (1998) *Proc. Natl. Acad. Sci., USA* 95, 13018-13023.

Dahlqvist, A., Ståhl, U., Lenman, M., Banas, A., Lee, M., Sandager, L., Ronne, H. and Stymne, S. (2000) *Proc. Natl. Acad. Sci., USA* 97, 6487-6492.

Gleave, A. (1992) Plant Molecular Biology 20, 1203-1207.

Lardizabal, K. D., Hawkins, D. J. and Thompson, G. A. (2001) DGAT2: A New Diacylglycerol Acyltransferase Gene Family. JBC 276 (42) 38862-38869.

Sandager, L., Gustavsson, M., Stahl, U., Dahlqvist, A., Wiberg, E., Banas, A., Lenman, M., Ronne, H., and Stymne, S. (2002) Storage lipid synthesis is non-essential in yeast. Journal of Biological Chemistry 277, 6478-6482

Sherman, F., Fink, G. R., and Hicks, J. B. (1986) Laboratory Course Manual for Methods in Yeast Genetics, Cold Spring Harbor Lab. Press, Plainview, N.Y.

Stålberg, K., Ellerström, M., Josefsson, L.-G., and Rask, L. (1993) Plant Molecular Biology 23, 671-683.

Ronne, H., Carlberg, M., Hu, G.-Z. and Nehlin, J. O. (1991) *Mol. Cell. Biol.* 11, 4876-5884.

Thomas, B. J. and Rothstein, R. (1989) *Cell* 56, 619-630.

We claim:

1. A method of increasing the total oil content in a plant or a tissue, organ, part, cell or propagation material thereof, comprising
   a) transgenically expressing in a plant or a tissue, organ, part, cell or propagation material thereof a polypeptide, wherein the polypeptide comprises the amino acid sequence as set forth in SEQ ID NO: 2; and
   b) selecting a transgenic plant, or a tissue, organ, part, cell or propagation material thereof in which the total oil content in the plant, tissue, organ, part, cell or propagation material thereof is increased as compared to the wild type.

2. The method of claim 1, wherein the polypeptide is the polypeptide as set forth in SEQ ID NO: 2.

3. The method of claim 1, wherein the plant is an oil crop.

4. The method of claim 1, wherein the total oil content in a seed of the transgenic plant is increased.

5. A transgenic expression cassette comprising a nucleic acid sequence under the control of a promoter which is functional in a plant or a tissue, organ, part or cell thereof, wherein the nucleic acid sequence is selected from the group consisting of
   a) a nucleic acid sequence comprising the nucleic acid sequence as set forth in SEQ ID NO: 1; and
   b) a nucleic acid sequence encoding a polypeptide comprising the amino acid level-to sequence as set forth in SEQ ID NO: 2; and wherein expression of the nucleic acid sequence results in increased total oil content in the plant or the tissue, organ, part, cell or propagation material thereof.

6. The transgenic expression cassette of claim 5, wherein the nucleic acid sequence is the nucleic acid sequence as set forth in SEQ ID NO: 1.

7. The transgenic expression cassette of claim 5, wherein the nucleic acid sequence is a nucleic acid sequence encoding the polypeptide as set forth in SEQ ID NO: 2.

8. The tranagenic expression cassette of claim 5, wherein the promoter is a seed-specific promoter.

9. A transgenic vector comprising the expression cassette of claim 5.

10. A transgenic plant or tissue, organ, part, cell or propagation material thereof, comprising the expression cassette of claim 5.

11. The transgenic plant of claim 10, wherein the plant is selected from the group consisting of *Borvago officinalis, Brassica campestris, Brassica napus, Brassica rapa, Cannabis sativa, Cart hamus tinctorius, Cocos nucWera, Crainbe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut, and almond.

12. A method for the production of oils, fats or free fatty acids comprising extracting oils, fats or free fatty acids from a transgenic plant or tissue, organ, part, cell or propagation material thereof, wherein the transgenic plant or tissue, organ, part, cell or propagation material thereof is transformed with a transgenic expression cassette comprising a nucleic acid sequence under the control of a promoter which is fractional in the plant or the tissue, organ, part or cell thereof, wherein the nucleic acid sequence is selected from the group consisting of
   a) a nucleic acid sequence comprising the nucleic acid sequence as set forth in SEQ ID NO: 1; and
   b) a nucleic acid sequence encoding a polypeptide comprising the amino acid sequence as set forth in SEQ ID NO: 2;
and wherein expression of the nucleic acid sequence results in increased total oil content in the plant or the tissue, organ, part, cell or propagation material thereof as compared to a wild type.

13. The method of claim 12, wherein the nucleic acid sequence is the nucleic acid sequence as set forth in SEQ ID NO: 1.

14. The method of claim 12, wherein the nucleic acid sequence is a nucleic acid sequence encoding the polypeptide as set forth in SEQ ID NO: 2.

15. A seed which is true breeding for an isolated nucleic acid molecule encoding a polypeptide comprising the amino acid sequence as set forth in SEQ ID NO: 2 wherein expression of the polypeptide results in increased total oil content in the seed as compared to a wild type seed.

16. The seed of claim 15, wherein the polypeptide is the polypeptide as set forth in SEQ ID NO: 2.

17. A method of producing a transgenic plant having increased total oil content as compared to a wild type variety of the plant, comprising the steps of:
   a) transforming a plant cell with an expression cassette comprising a nucleic acid sequence selected from the group consisting of
      i) a nucleic acid sequence comprising the nucleic acid sequence as set forth in SEQ ID NO: 1; and
      ii) a nucleic acid sequence encoding a polypeptide comprising the amino acid sequence as set forth in SEQ ID NO: 2;
   b) generating transgenic plants from the plant cell;
   c) screening the trausgenic plants for increased total oil content; and
   d) selecting transgenic plants that demonstrate increased total oil content as compared to the wild type.

18. The method of claim 17, wherein the nucleic acid sequence is the nucleic acid sequence as set forth in SEQ ID NO: 1.

19. The method of claim 17, wherein the nucleic acid sequence is a nucleic acid sequence encoding the polypeptide as set forth in SEQ ID NO: 2.

* * * * *

UNITED STATES PATENT AND TRADEMARK OFFICE
CERTIFICATE OF CORRECTION

PATENT NO. : 7,465,850 B2  Page 1 of 1
APPLICATION NO. : 10/519943
DATED : December 16, 2008
INVENTOR(S) : Martijn Gipmans et al.

It is certified that error appears in the above-identified patent and that said Letters Patent is hereby corrected as shown below:

In the Claims:

In Claim 5, in column 29, on line 57, "prising the amino acid level-to sequence as set forth in" should read -- prising the amino acid sequence as set forth in --.

In Claim 8, in column 30, on line 28, "8. The tranagenic expression cassette of claim 5, wherein" should read -- 8. The transgenic expression cassette of claim 5, wherein --.

In Claim 11, in column 30, on line 38, "*nabis sativa, Cart hamus tinctorius, Cocos nucWera, Crainbe*" should read -- "*nabis sativa, Carthamus tinctorius, Cocos nucifera, Crambe* --.

In Claim 12, in column 30, on line 51, "sequence under the control of a promoter which is fractional" should read -- sequence under the control of a promoter which is functional --.

Signed and Sealed this

Second Day of June, 2009

JOHN DOLL
*Acting Director of the United States Patent and Trademark Office*